United States Patent [19]

Pedersen

[11] Patent Number: 4,699,785
[45] Date of Patent: Oct. 13, 1987

[54] CELL LINE PRODUCING FELINE LEUKEMIA VIRUS

[75] Inventor: Niels C. Pedersen, Winters, Calif.

[73] Assignee: The Regents of the University of California, Berkeley, Calif.

[21] Appl. No.: 651,744

[22] Filed: Sep. 18, 1984

[51] Int. Cl.$^4$ .................. A61K 39/21; C12N 7/00; C12N 7/06; C12N 5/00
[52] U.S. Cl. ........................ 424/89; 435/235; 435/238; 435/240; 435/241
[58] Field of Search ............... 424/89; 435/240, 235, 435/236–238, 241, 68

[56] References Cited

U.S. PATENT DOCUMENTS

| | | | |
|---|---|---|---|
| 3,520,972 | 7/1970 | Smith et al. | 424/89 |
| 4,117,112 | 9/1978 | Jarrett et al. | 424/89 |
| 4,264,587 | 4/1981 | Pedersen et al. | 424/89 |
| 4,303,644 | 1/1981 | Davis | 424/89 |
| 4,434,157 | 2/1984 | Olsen | 424/89 |

OTHER PUBLICATIONS

Pedersen et al. (1978), Am. J. Vet. Res., 40:1120–1126.
Mathes et al. (1980), by Elsevier/North Holland, Inc., Hardy, Essex and McClelland, eds. Feline Leukemia Virus, vol. No. 4.
Lewis et al. (1981), Infection and Immunity, pp. 888–894.

*Primary Examiner*—Blondel Hazel
*Attorney, Agent, or Firm*—Bertram I. Rowland

[57] ABSTRACT

A novel feline fibroblastic cell line infected with Snyder-Theilen feline leukemia virus is provided. The cell line produces large amounts of FeLV when cultured in a medium free from serum supplement. The latter aspect is a substantial advantage since it reduces the expense of culturing and eliminates the need to separate serum from culture medium prior to preparing a vaccine.

Feline fibroblastic cell line FF64/280 was deposited at the American Type Culture Collection on Apr. 17, 1984, and granted accession no. VR 2085.

6 Claims, No Drawings

CELL LINE PRODUCING FELINE LEUKEMIA VIRUS

BACKGROUND OF THE INVENTION

1. Field of the Invention

Feline leukemia virus (FeLV) is a retrovirus consisting of three subgroups designated A, B and C. FeLV is infectious among cats and is responsible for chronic viremia as well as a number of specific disseases including lymphoplastic or aplastic anemia, myelosuppression, thymic atrophy, thrombocytopenia, and reproductive failure, e.g., abortion, fetal resorption, and stillbirths. Neoplastic manifestations of FeLV infection, such as lymphosarcoma, account for a small portion of the morbidity and mortality caused by FeLV. FeLV infection in cats also causes suppression of the immune system which exposes the animal to opportunistic infection from a variety of microorganisms.

While a number of approaches have been proposed for producing vaccines against FeLV, including the production of subunit vaccines, the preparation of killed and/or inactivated whole virus FeLV vaccines still offers many advantages, such as including the full repertoire of antigenic sites. The preparation of whole virus vaccines, however, requires a large supply of virus and that the virus be free from contaminating serum supplements, such as fetal calf serum, which are usually required for culture of the host cell culture.

Thus, it would be desirable to provide a large supply of feline leukemia virus which is easily purified to allow preparation of a vaccine. It would be particularly desirable to provide a FeLV-infected cell line which is capable of secreting large amounts of FeLV into a culture medium which is free from serum supplements.

2. Description of the Prior Art

Whole virus FeLV vaccines are described in the following references. Pedersen it al. (1978) Am. j. Vet. Res. 40:1120–1126; Mathes et al., in: "Feline Leukemia Virus," eds. Hardy et al., Elsevier North Holland, New York, N.Y. (1981) pp. 211–216; and Lewis et al. (1981) Infect. Immun. 34:888–894.

SUMMARY OF THE INVENTION

A novel feline fibroblastic cell line which is productively infected with Snyder-Theilen feline leukemia virus (FeLV) is provided. The cell line, designated FF64/280, has been deposited at the American Type Culture Collection (A.T.C.C.), 12301 Parklawn Drive, Rockville, MD 20852, having been assigned accession no. VR 2085. The cell line is capable of producing very large amounts of the infected virus in continuous culture, which virus may be separated from the growth medium and inactivated for use as a vaccine to protect a feline host against viremia and diseases associated with FeLV infection. Surprisingly, growth supplement, such as fetal calf seum or fetal bovine serum. Elimination of the serum supplement during periods when cultural fluids are harvested reduces the cost of production and facilitates purification of the culture medium prior to preparation of the vaccine by inactivation. The cell line is also suitable as a substrate for co-cutting other feline viruses. By simultaneously propagating one or more additional viruses, a single vaccine protecting against each of the viruses may be efficiently and economically prepared.

DESCRIPTION OF THE SPECIFIC EMBODIMENTS

The cell line of the present invention was developed by culturing small, full-thickness pieces of skin removed from a domestic cat (*Felis catus*) using a two millimeter dermis biopsy punch. The skin pieces were finely chopped and the cells dispersed with trypsin. After removal of the trypsin, the cells were placed into culture flasks containing a suitable medium: Eagles' MEM with 10% fetal bovine serum. Within 7 days, cell division had commenced, and by 28 days there was a confluent monolayer of epithelial and fibroblastic cells. The culture was continued for two passages over 14 days, and the epithelial cells died out leaving only the fibroblastic cells. This primary cell line was designated FF64.

The FF64 cell line was then infected with Snyder-Theilen FeLV (ST-FeLV) as follows. Buffy coat blood cells from a cat designated No. 280 chronically infected with Snyder-Theilen feline leukemia virus (ST-FeLV is the natural subgroup AB helper of Snyder-Theilen feline sarcoma virus) were co-cultured with the FF64 cells. The FF64 cells became infected with ST-FeLV, following which infection the cells began to divide at a greater rate and went into continuous passage.

The productively infected cell line, designated FF64/280, has several characteristics that make it desirable for FeLV vaccine production. The cell line is capable of secreting large amounts of ST-FeLV, typically greater than 1 mg/L of culture medium each 48 hours, often as much as 5 mg/L, and the high level of viral growth does not require continuous supplementation with serum. Additionally, the FF64/280 cell line can serve as a substrate for infection by other feline viruses, such as feline calicivirus, feline herpes virus, feline panleukopenia virus, and the like, allowing the simultaneous production of each of these viruses for use in vaccines. Conveniently, a single vaccine for all of the viruses may be prepared from the culture medium. Finally, the cell line may be stably maintained in continuous passage, or may be stored in lyophilized form.

Coinfection of cell line FF64/280 with other feline viruses may be accomplished as follows. Subconfluent monolayers of the cell line are infected with the desired viral stain(s), and the serum supplement withdrawn from the medium 24 hours later. The culture medium may then be harvested within 24 to 72 hours following the infection. By infecting separate cultures of the FF64/280 cell line with each of the additional viruses, it is possible to pool the separate cultural media at preselected ratios to obtain a final product including the desired immunogenic amounts of each viral strain.

To obtain whole virus from the FF64/280 cell line, the cell line is cultured in a conventional manner, preferably using a culture medium containing 5% fetal bovine serum. A suitable culture medium will include Eagles' MEM and 5% fetal bovine serum. The culturing may be performed in a conventional culture flasks, or in larger culture reactors intended for the mass culturing of mammalian cell culture.

When the cells in the culture reach a sufficiently high density, typically above about $10^7$ cells/ml, the medium may be replaced with serum free medium supplemented with about 1 μg/ml hydrocortisone phosphate. Hyudrocortisone supplmentation prevents any stress-induced reduction in virus yield resulting from the change in medium. The culture fluids may be harvested from 24 to 48 hours later, and the cells may continue to be fed with serum-free, hydrocortisone-supplemented medium through 1 to 2 more cycles of cell growth and cultural fluid harvest. The cells should then be passed into new culture vessels and be fed with serum-supplemented medium until confluency is again achieved. The virus harvesting cycles may then be repeated.

The FeLV virus, and other viruses, if any, may be harvested from the serum-free culture medium by separating the culture medium, either on a batch or continuous basis. Dead cells and other relatively large debris can be removed from the medium by filtration or low speed centrifugation, and the viral particles can then be concentrated from 20 to 200 fold, typically by filtration using a filter media having a molecular exclusion of about 100 kilodaltons. The concentrated culture medium will be free of cellular debris and serum supplement. The final concentration of ST-FeLV will usually be from about 60 to 600 μg/ml.

The concentrated FeLV virus may be attenuated or inactivated by various conventional techiques, such as heat, formalin, formaldehyde, ozone, psoralens, β-propiolactone, and the like. The method selected should render the virus noninfectious, while leaving the virus antigenically intact. Such methods are well known in the art and need not be described here in detail. When a combination of viruses are provided, the inactivation method should be selected to be compatible with each of the viruses. Preferred is the use of β-propiolactone which has been found effective with all of the feline viruses tested.

The inactivated virus or viruses may be combined in a variety of vaccine formulations for inoculation. The concentrations of FeLV will generally be from about 60 to 600 μg/dose, with concentrations of other viruses (if present) as follows: $10^5$ to $10^6$ HA units/dose of feline panleukopenia virus; $10^6$ to $10^7$ $TCID_{50}$/dose of feline calicivirus; and $10^4$ to $10^6$ $TCID_{50}$ dose of feline herpes virus. The vaccine may include a physiologically-acceptable carrier, which may be an inert carrier such as ionized water, phosphate-buffered saline, saline, or the like, or may be a physiologically-acceptable immunopotentiator (adjuvant) such as a mineral oil, vegetable oil, mineral salt, or the like. Conveniently, the prepared vaccines will be packaged in small vials holding sufficient vaccine for one dose and having a septum for inserting a hypodermic needle.

The vaccine may be administered subcutaneously, intramuscularly, or intraperitoneally. Usually, a specific dosage at a specific site will range from about 0.1 to 4 ml, where the total dosage will range from about 0.5 ml to 8 ml. The number of injections and their temporal facing may be varied, but usually 1 to 3 injections at 1 to 3 weeks intervals are effective.

The following examples are offered by way of illustration, not by way of limitation.

EXPERIMENTAL

1. Yield of FeLV

The effect of varying the composition of the culture medium on the yield of FeLV from FF64/280 was assessed as follows. The FF64/280 cell line was grown in eleven culture flasks having a basal medium including Eagles' minimal essential medium (MEM) supplemented with L-glutamine and fetal bovine serum (10%). The culture medium was replaced in all flasks, with three of the flasks not receiving the fetal bovine serum, and four of the flasks having the fetal bovine serum replaced with hydrocortisone (1 μg/ml). The results are set forth in Table 1.

TABLE 1

| Flask No. | FBS* | HC** | FeLV Yield (mg/l) Day 1 | Day 2 | Day 3 |
|---|---|---|---|---|---|
| 1 | + | − | 1.1 mg/l | 1.06 mg/l | 1.00 mg/l |
| 2 | + | − | 0.83 | 0.94 | 1.05 |
| 3 | + | − | 0.83 | 0.94 | 1.17 |
| 4 | + | − | 0.80 | 1.03 | 1.21 |
| 5 | − | − | 0.56 | 0.94 | 1.03 |
| 6 | − | − | 0.59 | 0.94 | 1.10 |
| 7 | − | − | 0.38 | 0.83 | 1.05 |
| 8 | − | + | 0.97 | 0.96 | 1.10 |
| 9 | − | + | 1.07 | 1.13 | 1.09 |
| 10 | − | + | 0.93 | 1.23 | 1.25 |
| 11 | − | + | 0.92 | 1.03 | 1.24 |

*"+" indicates that fetal bovine serum supplement added to medium.
**"+" indicates that hydrocortisone supplement added to medium.

The results in Table 1 indicate that cell line FF64/280, after an initial shock resulting from removal of fetal bovine serum from the culture medium, can produce FeLV at the same level in the absence of serum in the growth medium. Furthermore, the initial depression in production can be alleviated by adding hydrocortisone to the medium at the time that the serum is removed.

2. Efficacy of Vaccine

Cell line FF64/280 was grown to confluency in a basal medium containing Eagle's MEM with L-glutamine and 1 μg/ml hydrocortisone supplement, but free from serum. The culture medium was harvested and concentrated 200 fold in a millipore Pelicon apparatus. The concentrate was free from contaminating serum components, but retained about 99% of the viral gp70 and 27 activity, as measured by ELISA.

A vaccine was prepared from the culture medium concentrate by inactivation with 0.8% formaldehyde for 24 hours at 4° C., and addition of 0.3% ethylene malic anhydride at 1:1 vol:vol, or Freund's incomplete adjuvant at 1:1 vol:vol. Vaccine dosages (1 to 2 ml) having the equivalent viral content of 50 ml and 200 ml of the unconcentrated culture medium were prepared.

Eighty-four cats which were free from all clinical signs of FeLV infection were selected for testing of the vaccine. Different groups of the cats were injected with the vaccines having each of the adjuvants, while control groups were inoculated with the adjuvant alone. The vaccines were administered in 1 to 2 ml doses intramuscularly in the hind legs. Booster immunizations were given either three or six weeks later. The vaccination elicited moderate to high levels of antibodies to FeLV-gp70 and whole FeLV, as measured by ELISA.

One to two weeks after the final immunization, the cats were challenged with $10^7$ ST-FeLV transformed feline fibroblasts given subcutaneously between the shoulder blades. This challenge induced a systemic ST-FeLV viremia and a localized sarcoma at the site of inoculation. The growth rate of the sarcoma was directly relate with the level and persistence of the viremia. Cats that were resistant to viremia usually developed small rapidly regressing sarcomas at the site of inoculation, while cats that developed a persistent viremia usually succumbed from progressively growing tumors. The efficacy of the vaccine could therefore be determined by its ability to depress tumor growth as well as by its ability to suppress viremia Table 2 shows the results of individual experiments using the inactivated whole virus vaccine of the present invention and fibrosarcoma challenge. The data are summarized in Table 3, and comparisons are made between the performance of the whole FeLV vaccine of the present invention and natural and recombinantly produced gp 70 subunit vaccines. The natural FeLV-gp70 subunit vaccines were prepared by isolation of the glycoprotein from the virus, while the recombinant subunit vaccines were obtained from Cetus Corporation, Emeryville, CA. It is apparent from this data that the whole virus vaccine was effective in decreasing both tumor growth and viremia.

used as adjuvants. The immunogenicity of this vaccine was compared to a commonly used trivalent commercial vaccine (FVR-CP, Pittman-Moore Corporation) containing modified live FHV and FCV, and killed FPV. Antibody responses of cats vaccinated with the experimental quadrivalent vaccine were at least comparable to those induced by the commercial vaccine, and in the case of the FPV and FCV components, they were superior.

TABLE 2

| | | Disease Status (no. positive/total no.) | | | |
|---|---|---|---|---|---|
| Inoculation | Mean Peak Tumor Size | Regressing Tumors | Progressing Tumors | Undetectable or transient Viremia | Persistant Viremia |
| FICA* only | 169.0 g | 9/12 | 3/12 | 9/12 | 3/12 |
| Concentrated, Inactivated Virus & FICA | 38.0 g | 12/12 | 0/12 | 12/12 | 0/12 |
| FICA only | 659.0 g | 4/9 | 5/9 | 4/9 | 5/9 |
| 50 ml eq. Inactivated Virus & FICA | 295.0 g | 5/8 | 3/8 | 5/8 | 3/8 |
| 200 ml eq. Inactivated Virus & FICA | 173.0 g | 7/8 | 1/8 | 7/8 | 1/8 |
| FICA only | 223.0 g | 4/5 | 1/5 | 4/5 | 1/5 |
| 200 ml eq. Inactivated Virus & FICA | 35.0 g | 6/6 | 0/6 | 6/6 | 0/6 |
| EMA** only | 220.0 g | 10/12 | 2/12 | 10/12 | 2/12 |
| 50 ml eq. Inactivated Virus & EMA | 110.0 g | 11/12 | 1/12 | 11/12 | 1/12 |
| # EMA only | NA | NA | NA | 12/14 | 2/12 |
| # 50 ml eq. Inactivated Virus & EMA | NA | NA | NA | 11/12 | 1/12 |
| FICA only | 279.0 g | 2/13 | 11/13 | 1/13 | 12/13 |
| 250 ml eq. Inactivated Virus & EMA | 32.0 g | 5/5 | 0/5 | 5/5 | 0/5 |

*FICA: Freund's incomplete adjuvant.
**EMA: ethylene malic anhydride.
Challenged with R-FeLV (Rickard strain), all other trials were challenged with ST-FeLV.

TABLE 3

| Vaccine | Post challenge Persistent Viremia |
|---|---|
| Synthetic gp70 | |
| controls | 1/6 = 17% |
| vaccinates | 4/16 = 40% |
| Native gp70 | |
| controls | 5/25 = 20% |
| vaccinates | 9/22 = 41% |
| Inactivated FeLV from FF64/280 | |
| controls | 25/63 = 40% |
| vaccinates | |
| 50 ml equivalent | 5/32 = 15.6% |
| 200 ml equivalent | 1/31 = 3.2% |

3. Efficacy of Quadrivalent Vaccine

The efficacy of a quadrivalent FeLV/FPV/FHV/FCV vaccine was tested in cats. When formalin was used as the inactivator, only the FeLV and FPV were immunogenic. When β-propiolactone was used to inactivate the viruses, however, all 4 components were immunogenic. Tables 4–6 show the antibody responses to FPV, FHV, and FCV of cats vaccinated with a quadrivalent vaccine made from 200 ml of pooled media inactivated with β-propiolactone. The vaccines were given inititally when the kittens were 10 to 12 weeks of age and repeated 3 weeks later. Aluminum hydroxide gel and quil A (saponin) were

TABLE 4*

| | | FHV VN Antibody Titer Days Post Immunization | |
|---|---|---|---|
| Cat # | Vaccine | 0 | 35 |
| 3014 | commercial trivalent | 10 | 160 |
| 3017 | " | 0 | 80 |
| 3020 | " | 0 | 320 |
| 3022 | " | 0 | 160 |
| 3028 | " | 10 | 20 |
| 3032 | " | 0 | 160 |
| 3033 | " | 10 | 160 |
| 3036 | " | 0 | 80 |
| 3039 | " | 0 | 320 |
| 3044 | " | 10 | 640 |
| 3012 | quadrivalent | 0 | 40 |
| 3013 | " | 0 | 80 |
| 3018 | " | 0 | 160 |
| 3019 | " | 0 | 80 |
| 3023 | " | 0 | 20 |
| 3024 | " | 0 | 320 |
| 3030 | " | 0 | 40 |
| 3031 | " | 0 | 40 |
| 3034 | " | 0 | 40 |
| 3038 | " | 0 | 20 |
| 3040 | " | 0 | 40 |
| 3041 | " | 0 | 160 |
| 3051 | " | 0 | 20 |

TABLE 4*-continued

| Cat # | Vaccine | FHV VN Antibody Titer Days Post Immunization | |
|---|---|---|---|
| | | 0 | 35 |
| 3058 | " | 0 | 80 |

*Serum virus neutralizing (VN) antibody response against feline herpes virus (FHV) of cats immunized with 2 doses of quadrivalent (FeLV/FHV/FPV/FCV) or commercial trivalent (FHV/FPV/FCV) vaccines. Vaccines were given intramuscularly on days 0 and 21. VN antibody titers were expressed as reciprocals of the highest dilution of serum causing complete neutralization of 100 TCID$_{50}$ of FHV.

TABLE 5*

| Cat # | Vaccine | HI titers in serum-days post immunization | |
|---|---|---|---|
| | | 0 | 25 |
| 3014 | commercial | 0 | 160 |
| 3017 | " | 0 | 120 |
| 3020 | " | 0 | 10 |
| 3022 | " | 0 | 640 |
| 3028 | " | 0 | 640 |
| 3032 | " | 0 | 640 |
| 3033 | " | 0 | 80 |
| 3036 | " | 0 | 160 |
| 3039 | " | 0 | 320 |
| 3044 | " | 0 | 320 |
| 3012 | quadrivalent | 0 | 1280 |
| 3013 | " | 0 | 1280 |
| 3018 | " | 0 | 160 |
| 3019 | " | 0 | 160 |
| 3023 | " | 0 | 1280 |
| 3024 | " | 0 | 1280 |
| 3030 | " | 0 | 10 |
| 3031 | " | 0 | 320 |
| 3034 | " | 0 | 80 |
| 3038 | " | 0 | 320 |
| 3040 | " | 0 | 1280 |
| 3041 | " | 0 | 1280 |
| 3051 | " | 0 | 320 |
| 3058 | " | 0 | 40 |

*The antibody response against feline panleukopenia virus (FPV) of cats immunized with 2 doses of killed quadrivalent (FeLV/FHV/FPV/FCV) or commercial trivalent (FHV/FPV/FCV) vaccine. Vaccines were given intramuscularly on days 0 and 21. Antibody titers were expressed as the reciprocal of the serum dilution that inhibited the agglutination of rhesus red blood cells by 10 HA units of FPV.

TABLE 6*

| Cat # | Vaccine | FCV-2280 VN Antibody Titers Days After Start of Immunization | |
|---|---|---|---|
| | | 0 | 35 |
| 3014 | commercial trivalent | 0 | 0 |
| 3017 | " | 0 | 0 |
| 3020 | " | 0 | 0 |
| 3022 | " | 0 | 0 |
| 3033 | " | 0 | 0 |
| 3012 | quadrivalent | 0 | 20 |
| 3016 | " | 0 | 10 |
| 3035 | " | 0 | 20 |
| 3037 | " | 0 | 40 |
| 3043 | " | 0 | 10 |

TABLE 6*-continued

| Cat # | Vaccine | FCV-2280 VN Antibody Titers Days After Start of Immunization | |
|---|---|---|---|
| | | 0 | 35 |
| 3047 | " | 0 | 0 |

*Serum virus neutralizing antibody responses to FCV-2280 of cats immunized with 2 doses of quadrivalent (FeLV/FHV/FPV/FCV) or commercial trivalent (FHV/FPV/FCV) vaccines. Vaccines were given intramuscularly on days 0 and 21. Virus neutralizing antibody titers were expressed as the reciprocals of the highest serum dilutions that completely neutralized 100 TCID$_{50}$ of FCV-2280.
**FCV-2280 is a field isolate that is resistant to all commercial vaccines.

According to the present invention, a novel feline fibroblastic cell line infected with Snyder-Theilen feline leukemia virus has been found to produce large amounts of such virus in a culture medium free from serum supplement. The cell line serves as a particularly convenient source for obtaining the whole, live virus free from contaminating serum components. Inoculation with the inactivated virus has been shown to provide substantial protection in cats against subsequent challenge with FeLV.

Although the foregoing invention has been described in some detail by way of illustration and example for purposes of clarity of understanding, it will be obvious that certain changes and modifications may be practiced within the scope of the appended claims.

What is claimed is:

1. A fibroblast cell line infected with Snyder-Theilen feline leukemia virus, designated A.T.C.C. accession no. VR 2085.

2. A method for preparing a vaccine capable of protecting a cat against viremia resulting from infection by feline leukemia virus, said method comprising:
   obtaining whole, live feline leukemia virus from a fibroblastic cell line infected with Snyder-Theilen feline leukemia virus, designated A.T.C.C. accession no. VR 2085;
   inactivating the virus; and
   combining the inactivated virus in a physiologically-acceptable carrier.

3. A method for protecting a cat against viremia resulting from infection by feline leukemia virus, said method comprising administering to the cat a vaccine containing an amount of inactivated feline leukemia virus obtained from a cell line designated A.T.C.C. VR 2085, said amount being effective to elicit serum-neutralizing antibodies against the virus.

4. A method for producing a multivalent feline vaccine, said method comprising a propagating one or more different feline viruses on feline fibroblastic cell line FF64/280, A.T.C.C. designation no. VR 2085 in a suitable culture medium, collecting the medium which pg,19 contains feline leukemia virus in addition to the propagated virus(es), and inactivating the viruses in the culture medium to provide the vaccine.

5. A method as in claim 4, wherein the propagated virus(es) is at least one virus selected from the group consisting of feline calicivirus, feline panleukopenia virus, and feline herpes virus.

6. A method as in claim 4, wherein the virsu(es) is inactivated by treatment with β-propiolactone.

* * * * *